US012591938B1

(12) United States Patent
Yajaman et al.

(10) Patent No.: US 12,591,938 B1
(45) Date of Patent: Mar. 31, 2026

(54) ARTIFICIAL-INTELLIGENCE-BASED USER DATA VALIDATION

(71) Applicant: Express Scripts Strategic Development, Inc., St. Louis, MO (US)

(72) Inventors: Nikhil Dinesh Yajaman, Denton, TX (US); Morgan J. Finley, St Louis Park, MN (US); Micah Mclean, Gilbert, AZ (US); Anirban Chowdhury, Frisco, TX (US); Mantu Kumar, Jamshedpur (IN)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 18/901,375

(22) Filed: Sep. 30, 2024

(51) Int. Cl.
| | |
|---|---|
| *G06Q 40/08* | (2012.01) |
| *G06F 16/23* | (2019.01) |
| *G06Q 30/0601* | (2023.01) |
| *G16H 20/10* | (2018.01) |

(52) U.S. Cl.
CPC ....... *G06Q 40/082* (2025.08); *G06F 16/2358* (2019.01); *G06Q 30/0637* (2013.01); *G06Q 40/08* (2013.01); *G06Q 40/09* (2025.08); *G16H 20/10* (2018.01)

(58) Field of Classification Search
CPC ...... G06Q 40/08; G06Q 40/082; G06Q 40/09; G06Q 30/0637; G06F 16/2358; G16H 20/10
See application file for complete search history.

(56) References Cited

U.S. PATENT DOCUMENTS

| | | | |
|---|---|---|---|
| 7,286,984 B1 | 10/2007 | Gorin | |
| 7,356,168 B2 | 4/2008 | Tavares | |
| 8,504,380 B2 | 8/2013 | Broverman | |
| 8,601,030 B2 | 12/2013 | Bagchi | |
| 10,176,434 B2 | 1/2019 | Moghaddam | |
| 10,748,070 B2 | 8/2020 | Rajagopalan | |
| 10,991,457 B1 * | 4/2021 | Hallemeier | G16H 40/20 |
| 2004/0093261 A1 | 5/2004 | Jain | |
| 2008/0221886 A1 | 9/2008 | Colin | |
| 2009/0138266 A1 | 5/2009 | Nagae | |
| 2010/0088305 A1 | 4/2010 | Fournier | |
| 2014/0081652 A1 | 3/2014 | Klindworth | |
| 2017/0243134 A1 | 8/2017 | Housman | |
| 2018/0234108 A1 | 8/2018 | Fallon | |
| 2018/0293581 A1 | 10/2018 | Bansal | |
| 2019/0108470 A1 | 4/2019 | Jain | |
| 2022/0093080 A1 | 3/2022 | Kapralova | |
| 2022/0310261 A1 * | 9/2022 | Vodencarevic | G16H 50/50 |
| 2024/0267435 A1 * | 8/2024 | Wulf | G06N 5/04 |

* cited by examiner

*Primary Examiner* — Scott C Anderson
(74) *Attorney, Agent, or Firm* — Miller Johnson

(57) ABSTRACT

A method includes receiving an indication that a record has been updated and determining a confidence score. The method includes, in response to a determination that the confidence score has not met a threshold, filtering a set of communications. The method includes determining whether the record change has met one or more of a set of validity criteria. The method includes, in response to a determination that the user record change has not met the set of validity criteria, based on a first outcome of a set of reporting criteria, automatically generating a prompt with a first suggested revision of the first change. The method includes, in response to a determination that the record change has not met the set of validity criteria, based on a second outcome of the set of reporting criteria, automatically revising the first change with the first suggested revision.

20 Claims, 11 Drawing Sheets

Pallet Sizing And Pucking Device(s) — 206

Loading Device(s) — 208

Inspect Device(s) — 210

Unit of Use Device(s) — 212

Automated Dispensing Device(s) — 214

Manual Fulfillment Device(s) — 216

Review Devices — 218

Imaging Device(s) — 220

Cap Device(s) — 222

Accumulation Devices — 224

Packing Device(s) — 226

Literature Device(s) — 228

Unit of Use Packing Device(s) — 230

Mail Manifest Device(s) — 232

FIG. 2          112

ARTIFICIAL-INTELLIGENCE-BASED USER DATA VALIDATION

FIELD

The present disclosure relates to automated data validation and, more particularly, to machine learning systems for validation of entered data.

BACKGROUND

Recording, updating, and validating user data is an essential operation in many applications. Incorrect data can result in errors which cause inefficiencies such as increased human oversight and processing time. The correction and verification of user data is time-intensive and can quickly scale beyond the human capability to manually correct.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A method includes receiving an indication that a user record associated with a user has been updated with a first change. The method includes determining a confidence score that the first change is valid. The method includes, in response to a determination that the confidence score has not met a confidence threshold, filtering a set of communications associated with the user to create a subset of communications. Filtering includes determining whether a respective communication of the set of communications includes a communication topic related to the first change. The method includes determining, via an analysis of the subset of communications by a first machine learning model, whether the first change has met one or more of a set of validity criteria. A communication of the subset of communications includes a first portion, a second portion, and a third portion. The first portion and the third portion are analyzed by the first machine learning model before the second portion is analyzed. The method includes, in response to a determination that the first change has not met the set of validity criteria and based on a first outcome of a set of reporting criteria, automatically generating a prompt with a first suggested revision of the first change. The method includes, in response to a determination that the first change has not met the set of validity criteria and based on a second outcome of the set of reporting criteria, automatically revising the first change with the first suggested revision.

In other features, the method includes, based on the first outcome of the set of reporting criteria, receiving a verification input corresponding to the prompt. In other features, the method includes, in response to a modification input corresponding to the prompt, revising the first suggested revision. In other features, the method includes, in response to an approval input corresponding to the prompt, accepting the first suggested revision. In other features, the method includes, in response to a rejection input corresponding the prompt, rejecting the first suggested revision.

In other features, the confidence score is determined by a second machine learning model. The confidence score is based on a set of historical data associated with the user, including a current time of year, a level of novelty associated with the first change, a set of previous values associated with the user record, a set of dates associated with the set of previous values, and a quantity of deliveries associated with the set of previous values. In other features, the method includes updating a set of training data for the second machine learning model based on at least one of the confidence score, a user input corresponding to the prompt, or the first change.

In other features, the filtering is performed by a third machine learning model. In other features, the method includes, in response to a determination that the first change is valid, generating an indication that the first change has been verified, and automatically generating and transmitting a report associated with the first change. In other features, the method includes, in response to a determination that the confidence score has met a confidence threshold, generating an indication that the first change has been verified, and automatically generating and transmitting a report associated with the first change.

In other features, the method includes digitizing the subset of communications. Digitizing the subset of communications includes at least one of transcribing a respective communication, performing an analysis via machine vision on the respective communication, translating the communication, processing text, audio, video, or image files, or performing optical character recognition.

In other features, the set of reporting criteria includes a criterion that is met when a manufacturer associated with a product or service consumed by the user requires reports associated with the product or service to be transmitted to the manufacturer. In other features, the set of reporting criteria includes a criterion that is met when user data must be changed by an authorized agent. In other features, the set of reporting criteria includes a criterion that is met when a user is associated with a product or service that meets a set of restriction requirements.

In other features, the set of validity criteria includes a criterion that is met when a user requests the first change in a respective communication of the subset of communications and a criterion that is met when the first change matches a set of data in the respective communication. In other features, the method includes, in response to a determination that the first change has met the set of validity criteria, automatically preparing a physical product delivery.

In other features, the first portion includes a beginning portion of the communication of the subset of communications. In other features, the second portion includes a middle portion of the communication of the subset of communications. In other features, the third portion includes an end portion of the communication of the subset of communications.

A non-transitory computer-readable medium stores processor-executable instructions. The instructions include receiving an indication that a user record associated with a user has been updated with a first change. The instructions include determining a confidence score that the first change is valid. The instructions include, in response to a determination that the confidence score has not met a confidence threshold, filtering a set of communications associated with the user to create a subset of communications. Filtering includes determining whether a respective communication of the set of communications includes a communication topic related to the first change. The instructions include determining, via an analysis of the subset of communications by a first machine learning model, whether the first change has met one or more of a set of validity criteria. A communication of the subset of communications includes a first portion, a second portion, and a third portion. The first portion and the third portion are analyzed by the first machine learning model before the second portion is analyzed. The instructions include, in response to a determination that the first change has not met the set of validity criteria, based on a first outcome of a set of reporting criteria, automatically generating a prompt with a first suggested revision of the first change. The instructions include, in response to a determination that the first change has not met the set of validity criteria, based on a second outcome of the set of reporting criteria, automatically revising the first change with the first suggested revision.

In other features, the instructions include, based on the first outcome of the set of reporting criteria, receiving a verification input corresponding to the prompt. In other features, the instructions include, in response to a modification input corresponding to the prompt, revising the first suggested revision. In other features, the instructions include, in response to an approval input corresponding to the prompt, accepting the first suggested revision. In other features, the instructions include, in response to a rejection input corresponding the prompt, rejecting the first suggested revision.

In other features, the confidence score is determined by a second machine learning model. In other features, the confidence score is based on a set of historical data associated with the user, including a current time of year, a level of novelty associated with the first change, a set of previous values associated with the user record, a set of dates associated with the set of previous values, and a quantity of deliveries associated with the set of previous values. In other features, the instructions include, updating a set of training data for the second machine learning model based on at least one of the confidence score, a user input corresponding to the prompt, or the first change.

In other features, the instructions include, in response to a determination that the first change is valid, generating an indication that the first change has been verified and automatically generating and transmitting a report associated with the first change. In other features, the set of reporting criteria includes a criterion that is met when a manufacturer associated with a product or service consumed by the user requires reports associated with the product or service to be transmitted to the manufacturer. In other features, the set of reporting criteria includes a criterion that is met when user data must be changed by an authorized agent. In other features, the set of reporting criteria includes a criterion that is met when a user is associated with a product or service that meets a set of restriction requirements.

A system includes memory hardware configured to store instructions and processor hardware configured to execute instructions stored by the memory hardware. The instructions include receiving an indication that a user record associated with a user has been updated with a first change. The instructions include determining a confidence score that the first change is valid. The instructions include, in response to a determination that the confidence score has not met a confidence threshold, filtering a set of communications associated with the user to create a subset of communications. Filtering includes determining whether a respective communication of the set of communications includes a communication topic related to the first change. The instructions include determining, via an analysis of the subset of communications by a first machine learning model, whether the first change has met one or more of a set of validity criteria. A communication of the subset of communications includes a first portion, a second portion, and a third portion.

The first portion and the third portion are analyzed by the first machine learning model before the second portion is analyzed. The instructions include, in response to a determination that the first change has not met the set of validity criteria, based on a first outcome of a set of reporting criteria, automatically generating a prompt with a first suggested revision of the first change. The instructions include, in response to a determination that the first change has not met the set of validity criteria, based on a second outcome of the set of reporting criteria, automatically revising the first change with the first suggested revision.

In other features, the instructions include, based on the first outcome of the set of reporting criteria, receiving a verification input corresponding to the prompt. In other features, the instructions include, in response to a modification input corresponding to the prompt, revising the first suggested revision. In other features, the instructions include, in response to an approval input corresponding to the prompt, accepting the first suggested revision. In other features, the instructions include, in response to a rejection input corresponding the prompt, rejecting the first suggested revision.

In other features, the confidence score is determined by a second machine learning model. In other features, the confidence score is based on a set of historical data associated with the user, including a current time of year, a level of novelty associated with the first change, a set of previous values associated with the user record, a set of dates associated with the set of previous values, and a quantity of deliveries associated with the set of previous values. In other features, the instructions include, updating a set of training data for the second machine learning model based on at least one of the confidence score, a user input corresponding to the prompt, or the first change.

In other features, the instructions include in response to a determination that the first change is valid generating an indication that the first change has been verified, and automatically generating and transmitting a report associated with the first change.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Introduction

Figure 1:
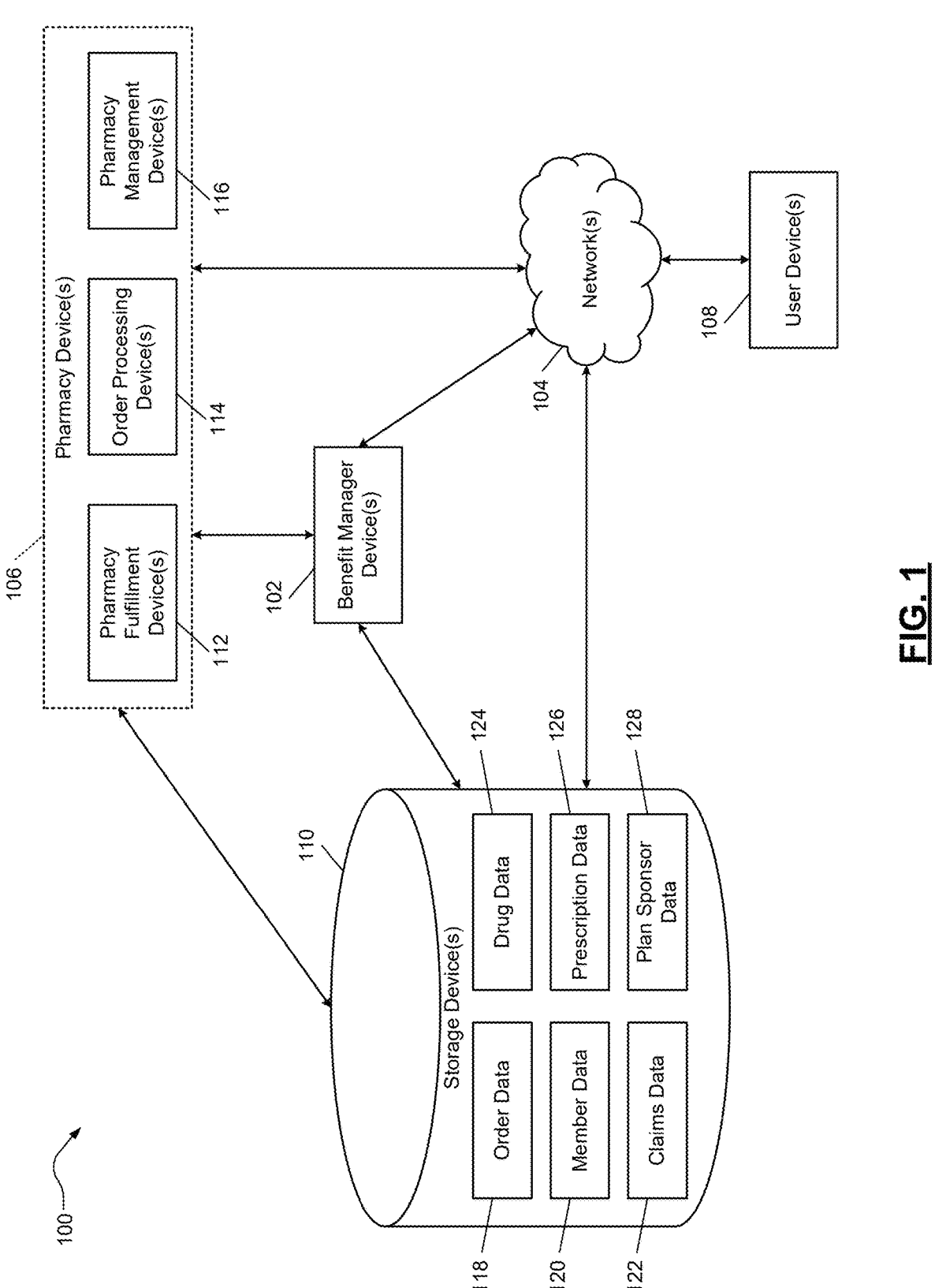
FIG. 1 is a functional block diagram of an example system including a high-volume pharmacy.

The present disclosure describes analyzing, updating, and verifying user data. While the present disclosure uses an example of user addresses and the delivery of physical goods such as prescription medication, the methods and systems described below can be applied to other forms of user data and other automated processes. As described below, errors can easily be introduced when inputting or updating user data. As one example, a user regularly receives (via mail and/or other physical delivery) a physical product (such as a prescribed drug, food, and/or other consumable good). The user data associated with the user includes the user's name, address, and/or other details which may require updating. The user may update their address once, rarely (for example, if the user receives deliveries while on vacation), or at regular intervals (for example, if the user regularly visits a secondary address for a portion of the year). Each of these update events can introduce error.

In some implementations, user data is updated via an agent (such as a doctor, pharmacist, nurse, call-center operator, and/or other authorized individual). In some implementations, user data can be updated via audio communication with an agent or automated telephone system, submitted paper forms, speech-to-text interfaces, video conferencing, a text chat interface with an agent, and/or a digital user interface of an application (such as a digital form with drop down menus, fillable text, and/or other user interface elements). Regardless of input method, error can be introduced in a variety of ways. For example, miscommunications between the user and the agent, errors made by either the user or the agent in a user interface (for example, mis-clicks or taps, accidental scrolling, and/or unoptimized user interfaces that result in the selection of an incorrect address), and/or programming errors in the user interface or application that result in the wrong address selection despite correct human operation.

Therefore, a system and method are needed to reduce error and to verify user data. In some implementations, user communications (such as call records, text chat records, video recordings, and/or paper communications) are stored and associated with the user. The current user data (in particular the changed user data) is compared to previous versions of the user data for anomalies at regular intervals, such as when user data is updated, account action is required (such as an upcoming shipment of goods), and/or a time based interval (such as daily, monthly, and/or semi-annually). If an anomaly is detected (such as a difference detected between current and previous versions of the user data-like an address change), the user data is reviewed and the anomaly (the updated data) is given a confidence score. In some implementations, when the confidence score is above a threshold (for example, the system is confident that the data change is correct or that no further action is required for this particular user data) no further processing occurs. In some implementations, the confidence score is used as an indicator of predicted accuracy and reintroduced as machine learning training feedback.

User communication records are reviewed to determine whether the communication records confirm the anomalous user data. In some implementations, the user communications are filtered by topic (for example, filtering out communications that do not relate to the anomalous data). The remaining communications are digitized and analyzed using one or more large language models (LLMs) to determine whether the communications confirm the user data change. In some implementations, digitization includes, for example, transcribing the communication using speech-to-text algorithms or machine learning models, translating the communication, using optical character recognition on the communication, and/or analyzing the communication with machine vision (for example, to translate non-spoken languages like American Sign Language to English text). In some implementations, the data anomaly (the change in user data) can be confirmed or corrected based on the analyzed communications automatically, or can be flagged for further human review and correction. In some implementations, a report is automatically generated and sent based on the communications and any suggested (or performed) updates to the data corresponding to the data anomaly.

As a first example, a user regularly receives a prescribed drug. The user calls an agent to update the shipment address to a hotel at which the user is staying for vacation. The agent inputs the address incorrectly into an address database interface. Before shipping the drug, the system notes that a new address has been saved and that the new address does not match the previous (or any previous) shipment address. The scoring model generates a low confidence score (indicating that the new address is likely an error), and all communications (such as calls) to the agent are filtered based on topic (so that only communications related to scheduling, shipments, and/or addresses remain). In some implementations, communications that occurred between the current shipment and the most previous shipment are considered. In some implementations, communications that occurred during a time interval are considered (such as the past week, month, and/or year). The remaining calls are transcribed and analyzed by an LLM. The LLM determines that while the user requested a new address, the listed address is not correct. The address is corrected automatically (or if necessary-reported for manual correction) and the change is saved and used as training data for the scoring model.

As another example, a patient receives a prescription drug by mail every month. The user spends the first half of the year in Ohio and the second half of the year in California and regularly changes (via text chat with an agent) the shipping address between the two locations. Before shipping the drug, the system indicates that the user address has been updated (from Ohio to California). Next, the scoring model generates a high confidence score that the address change is correct (based on the history of the user regularly changing the shipping address to the California address around this time of year). The system filters the text chat communications by topic. The filtered communications are analyzed and it is determined that the new address is correct (for example because the address exactly matches the text communications and the previous address). In some implementations, no further action is taken. In some implementations, the address is flagged as confirmed.

As another example, a user has been prescribed a new medication and has been asked to report on the symptoms. The user calls an agent to report adverse side effects. The agent records the symptom. At regular intervals, the system checks for records of adverse effects. The user communications are filtered to topics related to the new medication and its symptoms. The communications are then transcribed and analyzed by the LLM to determine whether an adverse effect was reported. If an adverse effect is reported, the system automatically generates and/or sends a report regarding the adverse effect.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug.

The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network (network 104), multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, age, date of birth, address (including city, state, and zip code), telephone number, e-mail address, medical history, prescription drug history, etc. In various implementations, the prescription drug history may include a prior authorization claim history-including the total number of prior authorization claims, approved prior authorization claims, and denied prior authorization claims. In various implementations, the prescription drug history may include previously filled claims for the member, including a date of each filled claim, a dosage of each filled claim, the drug type for each filled claim, a prescriber associated with each filled claim, and whether the drug associated with each claim is on a formulary (e.g., a list of covered medication).

In various implementations, the medical history may include whether and/or how well each member adhered to one or more specific therapies. The member data 120 may also include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. In various implementations, the member data 120 may include an eligibility period for each member. For example, the eligibility period may include how long each member is eligible for coverage under the sponsored plan. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member). In various implementations, the claims data 122 may include a percentage of prior authorization cases for each prescriber that have been denied, and a percentage of prior authorization cases for each prescriber that have been approved.

The drug data 124 may include drug name (e.g., technical name and/or common name), other names by which the drug is known, active ingredients, an image of the drug (such as in pill form), etc. The drug data 124 may include information associated with a single medication or multiple medications. For example, the drug data 124 may include a numerical identifier for each drug, such as the U.S. Food and Drug Administration's (FDA) National Drug Code (NDC) for each drug.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
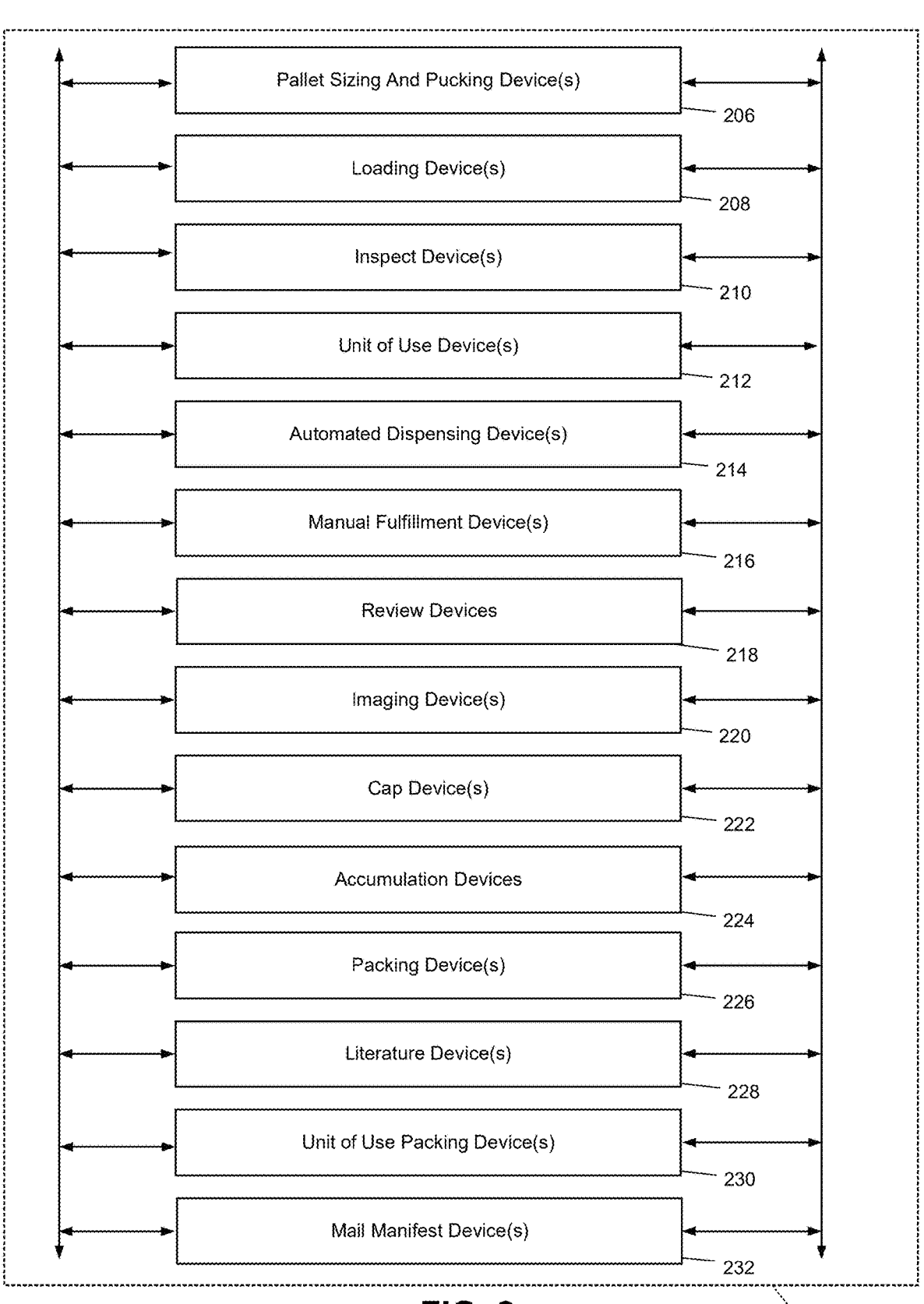
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing device(s) 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
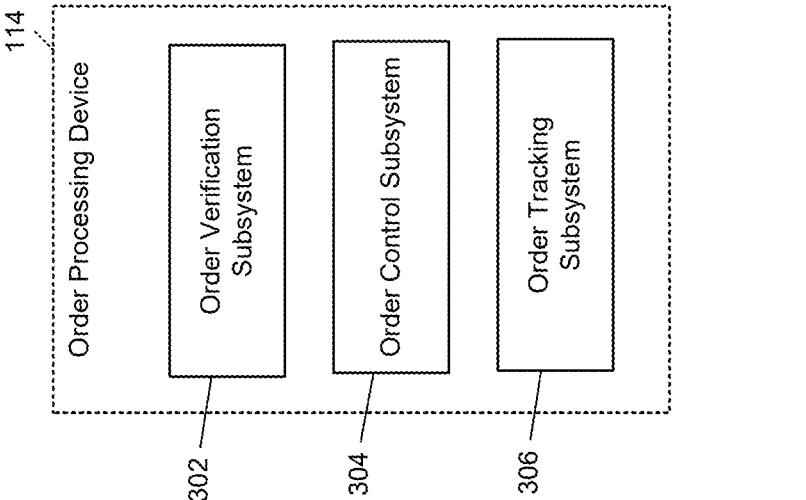
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Block Diagram

Figure 4:
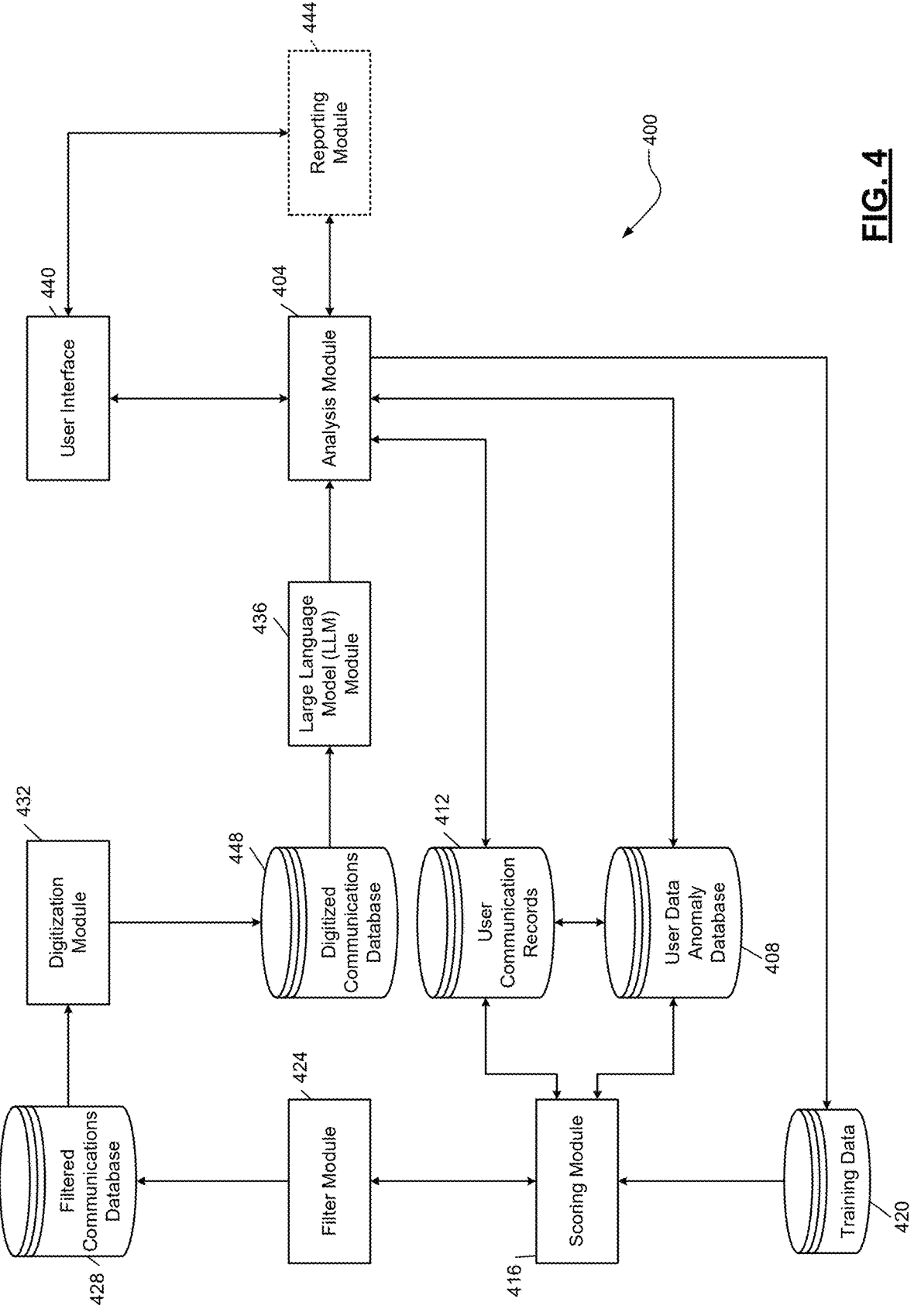
FIG. 4 is a block diagram of an example system for validating user data.

FIG. 4 is a block diagram of an example system for validating user data. User communication records 412 store communication data (for example, chat logs, call records, call recordings, and/or scans of physical communication records) associated with users. User data anomaly database 408 includes a record of user data, such as current and previous versions of user data (for example, a current address and all previous addresses associated with a user). User data anomaly database 408 indicates whether a user record has been updated. Analysis module 404 updates data stored in: user communication records 412 (for example, after a communication is received), user data anomaly database 408 (for example, at a regular interval, after user data is updated, and/or a time period before a product delivery), and training data 420 (for example, after system 400 has validated a user data change).

Scoring module 416 includes a machine learning model that generates a confidence score for the data anomaly. The confidence score indicates how likely it is that the data anomaly (the latest version of a user record stored in user data anomaly database 408) is correct. The confidence score is based on historical user data including patterns in the user data such as update frequency, the time of year (day, and/or week) of the update, the time of previous updates, a quantity or type services or products delivered, and/or a duration that the user data was set to a particular value. In some implementations, the scoring module generates a confidence score for a change of address by considering the quantity of deliveries of a product associated with a previous address compared to the new address, whether the new address has been used before (novelty of the address), whether the user frequently updates their address, whether address updates follow a pattern (such a seasonality where the user regularly changes address based on the time of year), a time year, etc. In some implementations, if a user data anomaly is associated with a confidence score that meets a confidence threshold, further analysis by the system is not required, and the anomaly is automatically resolved by analysis module 404 and/or flagged for human review via reporting module 444 (based on whether a set of reporting criteria are met). In some implementations, if the confidence score meets the confidence threshold, the data anomaly is still analyzed by the system 400.

The machine learning model of scoring module 416 is trained via training data 420. Training can include supervised learning, active learning, reinforcement learning, unsupervised learning, feature learning, and/or other training methods. Training data 420 is updated (by analysis module 404) with the results associated with generated confidence scores from scoring module 416. In some implementations, training data 420 includes analysis from large language model (LLM) module 436 and/or human verification (such as approval, rejection, and/or additional modification) of a suggested change or verification generated by LLM module 436. Human verification can be received via user interface 440 in response to prompts and/or reports generated by reporting module 444. In some implementations, training data 420 includes data related to frequent errors or patterns of errors by specific agents, users, and/or by specific applications or user interface elements.

Filter module 424 includes an LLM and/or natural language processing model to filter records from user communication records 412 by topic (such as a topic that is related to the user data anomaly). In some implementations, filter module 424 filters communications based on an age of a communication or whether the communication occurred during a specific time period before filtering the communications by topic. In some implementations, filter module 424 reviews communications that have occurred since a previous shipment, or over a rolling time period from the current time (such as the past week, month, or year). In some implementations, user communication records 412 does not transmit communication records to scoring module 416 and filter module 424 that are outside the specified date range. As an example, if the user data anomaly is related to an address change, the filter will only allow communication records of conversations discussing addresses, delivery updates, and/or shipping information since a most recent shipment. Communications that are topically related to the data anomaly and within the specified time period are stored in filtered communications database 428. In some implementations, filter module 424 filters all communications (for example, there are no communications topically related to the anomaly and/or there are no communications within the selected time period) and no additional analysis occurs and an alert is generated.

Digitization module 432 transcribes audio communication records, digitizes written communication records (such as image files) via optical character recognition, translates communications, performs machine vision processing of video (for example for non-verbal languages), and/or performs processing on communication records in filtered communications database 428. In some implementations, digitization increases digital readability for LLMs and increases LLM accuracy. Digitized communications are stored in digitized communications database 448 before being processed by LLM module 436. LLM module 436 analyzes the digitized communications to determine whether information related to the data change is contained within the communications and whether the data change is correct (also described as valid) based on the information within the communications. For example, LLM module 436 determines whether a user initiated a change to their shipping address, and if so, whether the new shipping address stored in user data anomaly database 408 is accurate.

Often the most relevant portion of a communication (for example, the portion including an address change or other data update information) is at the beginning or end of a communication. In some implementations, a beginning portion and an end portion of a communication are analyzed before a middle portion. In some implementations, the beginning portion and end portion of all communications are analyzed before the corresponding middle portions. In some implementations, an entire communication is analyzed starting with a beginning portion and an end portion before analyzing a middle portion and before moving to a next communication.

In some implementations, the beginning portion is determined by a percentage of the total communication length (for example the first 5-45%). In some implementations, the beginning portion is a determined by a set length (such as the first few minutes or seconds). In some implementations, the end portion is determined by a percentage of the communication (for example, the last 5-45%). In some implementations, the end portion is determined by a set length (such as the last few minutes or seconds). In some implementations, the middle portion is defined by the remaining portion of communication that is not determined to be a beginning or end portion.

In some implementations, LLM module 436 provides the LLM a prompt to determine which communications are related to the anomaly or which communication confirms the anomaly. In some implementations, only portions of the communications are passed to the LLM. In some implementations, the portions passed to the LLM are determined by cosine distance. If a portion of a communication is above a threshold cosine distance, it is passed to the LLM for analysis. For example, the first 60 seconds and last 60 seconds of a communication are analyzed (the beginning and end portions), then the remaining portions of the communications are divided into sentences and then sentences that are similar to the prompt are passed to the LLM.

In some implementations, LLM module 436 compares an address (or other user data) found in a communication to a current address (such as the currently saved address) using the Levenshtein algorithm. In some implementations, if the Levenshtein distance is above or below a threshold distance, the data is then passed to the LLM.

In some implementations, LLM module 436 prioritizes communications that are associated with one or more data flags (for example, tags that indicate a communication is related to patient verification, order scheduling, and/or address verification). In some implementations, data flags are added by agents after the communication occurs.

In some implementations, LLM module 436 determines whether the data anomaly is valid based on a set of criteria (such as whether the user has requested a change in the communication records and/or whether the change matches the contents of the communications). In some implementations, if LLM module 436 determines that the data anomaly is not correct, LLM module 436 generates a suggested update to the data anomaly.

The analysis of LLM module 436 is then sent to analysis module 404. Based on whether one or more of a set of review and/or reporting criteria are met (particularly based an outcome of which criterion are met and which are not met) analysis module 404 automatically updates the user record (for example, if the address was incorrect), and/or generates and transmits a report for review by an authorized agent (for example, via user interface 440). In some implementations, the report includes a prompt for the authorized agent to accept, reject, or modify the suggested update or to verify the data anomaly. In some implementations, the set of reporting criteria includes a criterion that is met when there are regulations governing address changes based on the product or service to be delivered, a criterion related to the value of the confidence score (such as whether the confidence score is below a threshold), and/or a requirement that data changes be approved by an authorized agent. In some implementations, if the analysis from LLM module 436 confirms that the data change is verified, a report is automatically generated and transmitted. In some implementations, a report of a verified data anomaly is generated via reporting module 444 based on a requirement that the data change be reported to a third party. For example, in some implementations, the product deliverer (such as a doctor or pharmacist) may be required to report user feedback (such as reviews or symptoms) to the product manufacturer.

Flowchart

Figure 5A:
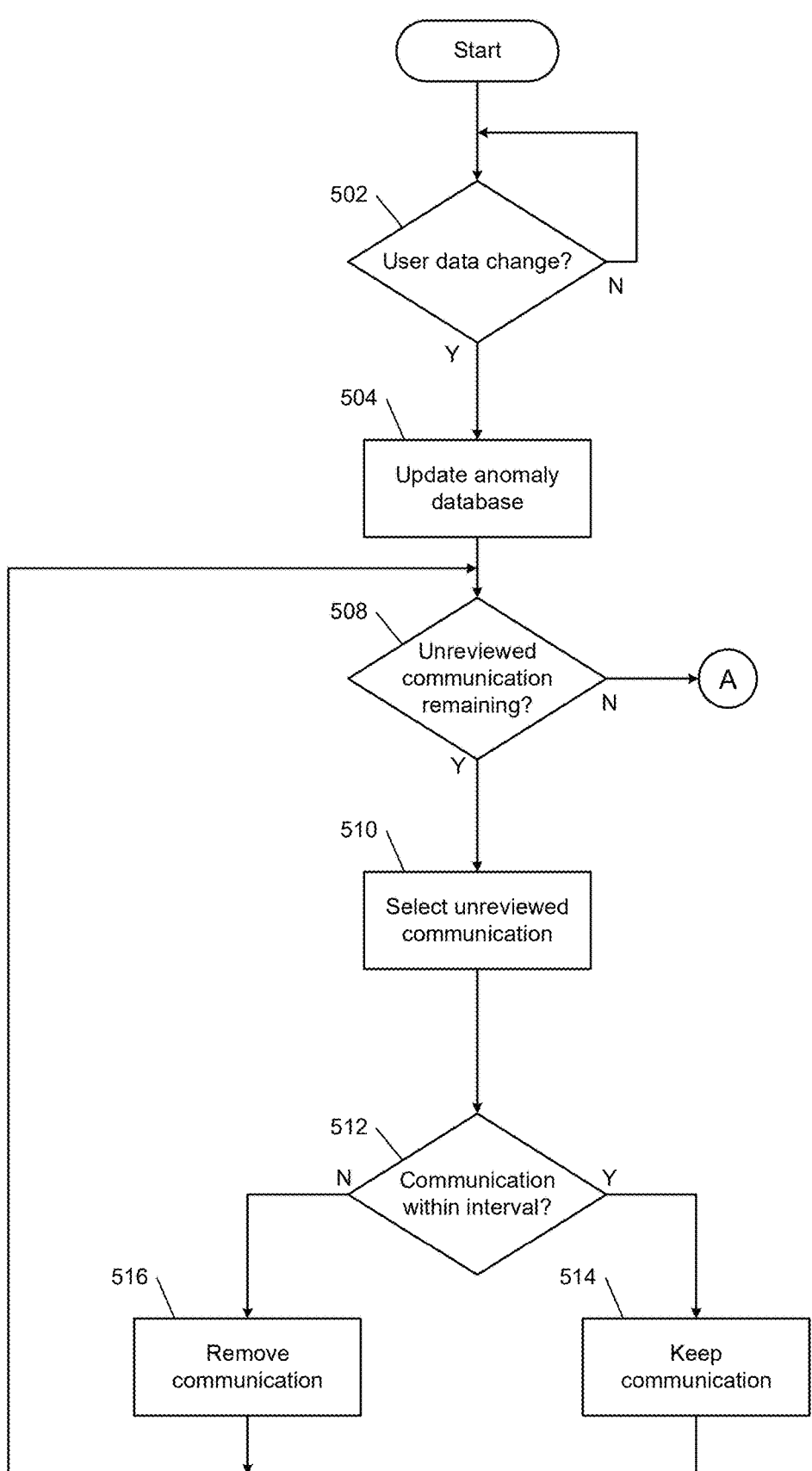
FIGS. 5A-5C are a flowchart of an example method for validating user data.
Figure 5B:
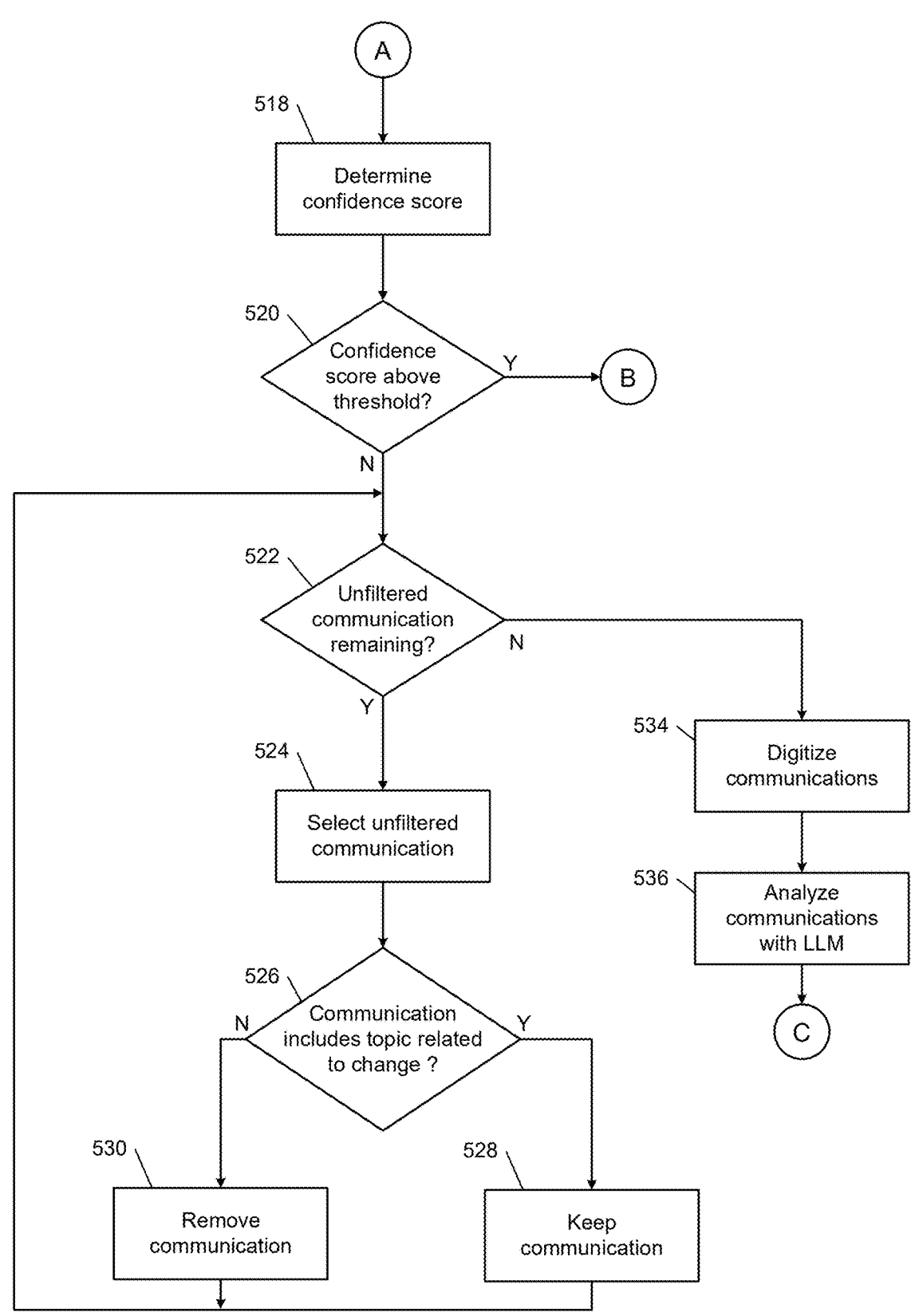
Figure 5C:
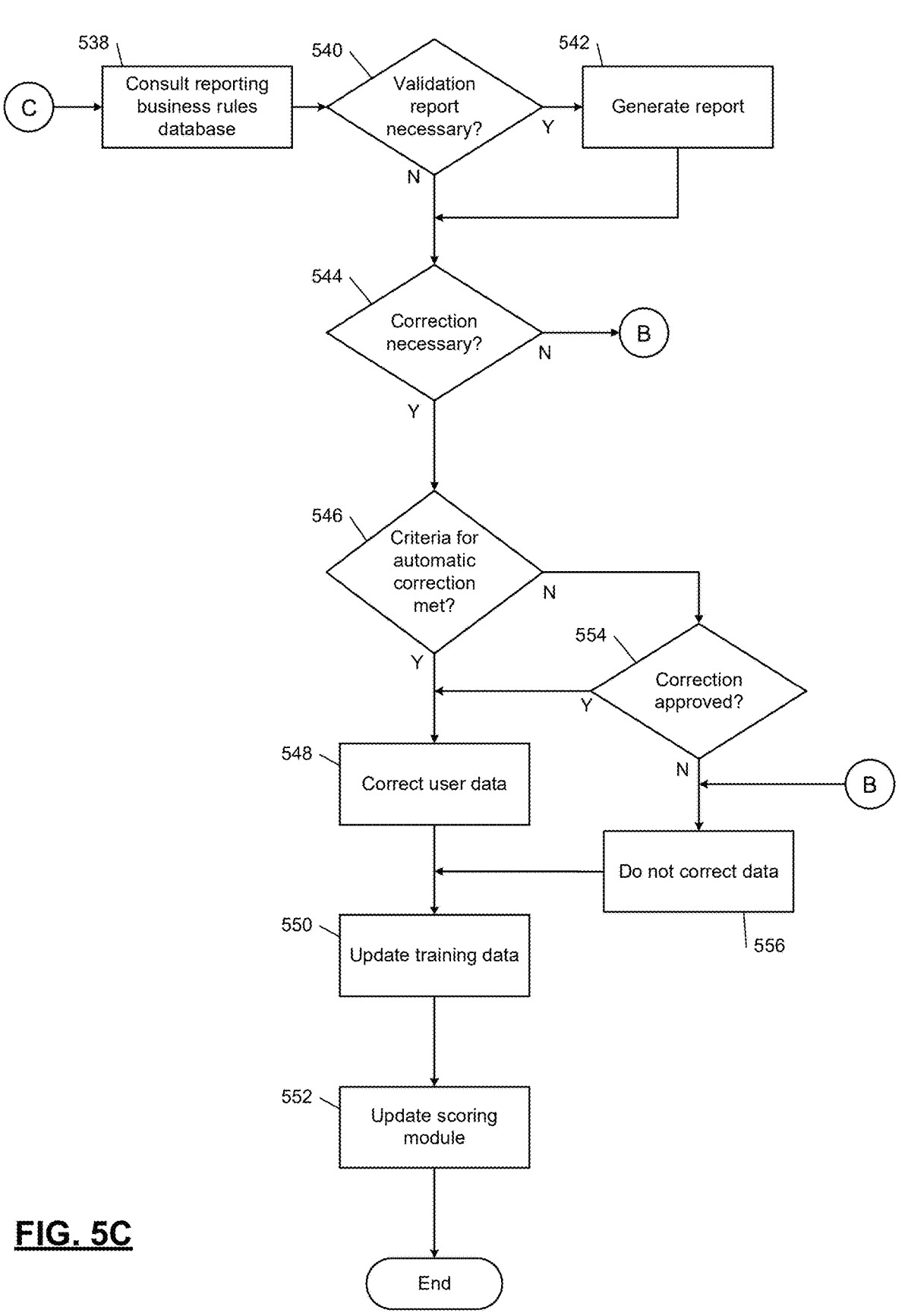

FIGS. 5A-5C are a flowchart of an example method for validating user data. The method begins at 502 and control determines whether a user data change has occurred (for example, whether a user address has been updated). If no user data change occurred, control remains at 502. If a change is detected, control continues to 504. In some implementations, the method starts after a set time interval has elapsed (for example, based on shipping intervals, weekly, and/or monthly). At 504, control updates the anomaly database with the user data change. At 508, control determines if there are unreviewed communications. If there are no unreviewed communications remaining, control transfers to 518. If there are unreviewed communications remaining, control transfers to 510. At 510, control selects one of the unreviewed communications. At 512, control determines whether a communication occurred within a time interval (for example, since a previous shipment, the last week, the last month, and/or the last year). If the communication is within the time interval, control transfers to 514, and the communication is kept for further analysis (for example by scoring module 416 and filter module 424). If the communication is not within the time interval, control transfers to 516 and the communication is not kept for additional analysis. After 514 and/or 516, control returns to 508.

At 518, control determines a confidence score. The confidence score is a representation of an estimated confidence that the user data change is accurate. At 520, control determines whether the confidence score is above a threshold. If the confidence score is above the threshold, control transfers to 556. If the confidence score is not above the threshold, control transfers to 522. At 522, control determines whether there are communications that have not been filtered by topic. If there are no remaining unfiltered communications, control transfers to 534. If there are remaining unfiltered communications, control transfers to 524. At 524, control selects one of the unfiltered communications. At 526, the selected communication is analyzed to determine whether the communication includes a topic related to the user data change. If the communication includes a related topic, control transfers to 528. If the communication does not include a related topic, control transfers to 530. At 528, the communication is kept for additional analysis (for example by digitization module 432 and LLM module 436). At 530, the communication is not kept for additional analysis. After 528 and/or 530 control returns to 522.

At 534, control digitizes the remaining communications (communications that include a topic related to the data change and are from the required time interval). In some implementations, digitization includes processing, machine vision analysis, translating, transcribing, and/or optical character recognition of communication records to increase LLM efficiency and/or accuracy. At 536 the filtered communications are analyzed with an LLM to determine whether the data change is valid. If the data change is not valid, the LLM generates a suggested update to the data change. After 536, control continues to 538.

At 538, control consults a business rules database. In some implementations, the business rules database is included in reporting module 444. At 540, control determines whether the suggested update to the data change and/or a verification of accuracy of the data change must be reported based on the business rules database. If the suggested update must be reported, control transfers to 542 where a report is automatically generated and transmitted. If it is not necessary for the suggested update and/or verification to be reported, control transfers to 544. At 544, control determines if a correction (applying the suggested update) to the data change is necessary (for example, the change should not have been made and/or the change includes inaccurate data). If no update is necessary, control transfers to 556. If a change is necessary, control transfers to 546.

At 546, control determines if a set of criteria for automatic correction of the data has been met. If yes, control transfers to 548 and corrects the user data (using the suggested update). If not, control transfers to 554. At 554 control determines if the suggested update has been approved (for example via user input in response to a report and/or prompt). If the suggested update have been approved, control transfers to 548 and the suggested update is applied to the data change. If the suggested update has not been approved, control transfers to 556 and control does apply the suggested update to the data change. After 556 and/or 548 control continues to 550. At 550, control updates the training data that is used to generate the confidence score. In some implementations, the updated training data includes the LLM suggested update, user input corresponding to approval, modification, or rejection of the suggested change, and other data related to the user record and data change. At 552, control updates the scoring module based on the updated training data and control ends.

Machine Learning

Figure 6:
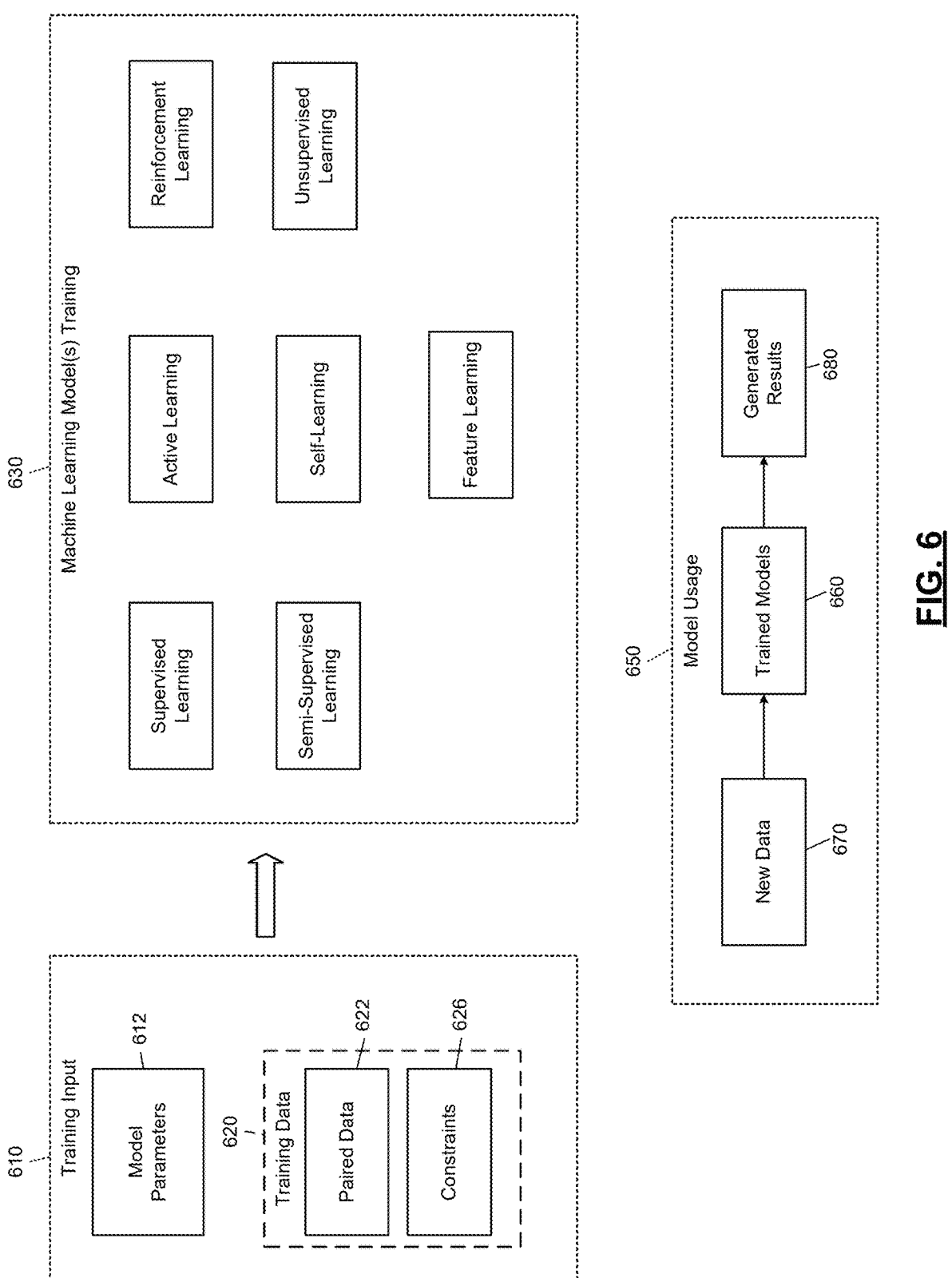
FIG. 6 is a functional block diagram of an example of machine learning model training and usage.

FIG. 6 is a block diagram of an example service that may be deployed above. Training input 610 includes model parameters 612 and training data 620, which may include paired training data sets 622 (e.g., input-output training pairs) and constraints 626. Model parameters 612 represents storing and/or providing the parameters or coefficients of corresponding ones of machine learning models. During training, the model parameters 612 are adapted based on the input-output training pairs of the paired training data sets 622. After the model parameters 612 are adapted (after training), the parameters are used in 650 by trained models 660 to implement the trained machine learning models on a set of new data 670.

Training data 620 optionally includes constraints 626 which may define the constraints of a given member's information features. The paired training data sets 622 optionally include sets of input-output pairs, such as pairs of a plurality of member preferences and features of entities associated with providers. Some components of training input 610 may be stored separately at a different off-site facility or facilities than other components.

Machine learning model(s) training 630 trains one or more machine learning techniques based on the sets of input-output pairs of paired training data sets 622. For example, the model training 630 may train the machine learning (ML) model parameters 612 by minimizing a loss function based on one or more ground-truth data. The model training 630 may include supervised learning, semi-supervised learning, active learning, self-learning, feature learning, reinforcement learning, and unsupervised learning.

The ML models can include any one or combination of classifiers or neural networks, such as an artificial neural network, a convolutional neural network, an adversarial network, a generative adversarial network, a deep feed forward network, a radial basis network, a recurrent neural network, a long/short term memory network, a gated recurrent unit, an auto encoder, a variational autoencoder, a denoising autoencoder, a sparse autoencoder, a Markov chain, a Hopfield network, a Boltzmann machine, a restricted Boltzmann machine, a deep belief network, a deep convolutional network, a deconvolutional network, a deep convolutional inverse graphics network, a liquid state machine, an extreme learning machine, an echo state network, a deep residual network, a Kohonen network, a support vector machine, a neural Turing machine, etc.

Particularly, a first ML model of the ML models can be applied to a training batch of member preferences to estimate or generate a prediction of provider choice for a particular member. In some implementations, a derivative of a loss function is computed based on a comparison of an estimate with ground truth entities, and parameters of the first ML model are updated based on the computed derivative of the loss function. The result of minimizing the loss function for multiple sets of training data trains, adapts, or optimizes the model parameters 612 of the corresponding first ML model. In this way, the first ML model is trained to establish a relationship between member data and member selections.

After the machine learning models are trained, the set of new data 670, including one or more sets of features for members, are received and/or derived from a document being accessed from the storage device 110 or training data 420. The first trained machine learning model may be applied to the set of new data 670 to generate results 680 (such as a prediction).

Figure 7:
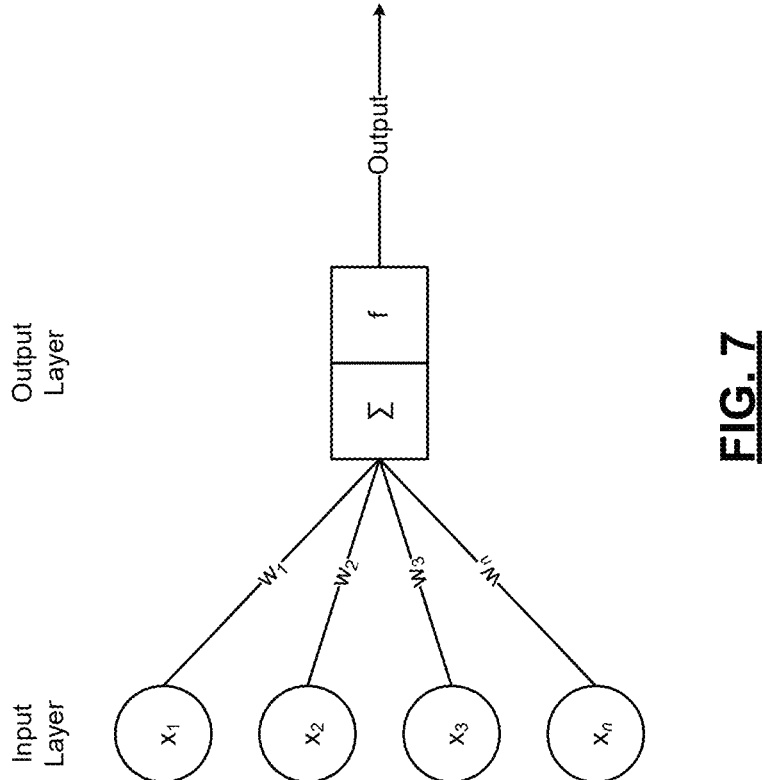
FIG. 7 is a functional block diagram of an example neural network.

FIG. 7 is a graphical representation of an example neural network with no hidden layers for implementing a machine learning module. In machine learning, a neural network—or an artificial neural network—is a network or circuit of artificial neurons or nodes having at least an input layer and an output layer. In various implementations, neural networks may also have one or more hidden layers. Neural networks may be used in deep learning applications to allow computer systems to solve artificial intelligence problems—such as problems in predictive modeling, pattern recognition, and dynamic control systems.

FIG. 7 shows a neural network without any hidden layers. The neural network of FIG. 7 may also be referred to as a single-layer perceptron. The neural network of FIG. 7 is shown with an input layer including n nodes, labeled $x_1$, $x_2$, $x_3$, and $x_n$. While only four nodes are illustrated in FIG. 7, the input layer may have any number of nodes. In various implementations, each node may represent any numerical value. For example, each node may represent a numerical value in a range of between 0 and 1. So, for example, the nodes of the input layer could be expressed in interval notation as: $x_1 \in [0,1]$, $x_2 \in [0,1]$, $x_3 \in [0,1]$, and $x_n \in [0,1]$. In various implementations, the input variables to a neural network may be expressed as a vector i having n dimensions. In the example of FIG. 7, input vector i may be represented by equation (1) below:

$$i = (x_1, x_2, x_3, x_n) \tag{1}$$

Each of the nodes may be multiplied by a weight—represented by $w_1$, $w_2$, $w_3$, and $w_n$ in FIG. 7—before being fed into a node in the next layer. In FIG. 7, because there are no hidden layers, the next layer is the output layer. For simplicity of illustration, only a single node is shown in the output layer of FIG. 7. However, the output layer may include any number of nodes.

At the node in the next layer, the inputs of the node are summed. Thus, because the inputs of the node in the output layer of FIG. 7 are the numerical value of each of the nodes of the previous layer multiplied by a weight, the summation Σ may be represented by equation (2) below:

$$\Sigma = x_1 w_1 + x_2 w_2 + x_3 w_3 + x_n w_n \qquad (2)$$

In various implementations, a bias b may be added to the nodes x of the previous layer after they have been multiplied by a weight w. For example, if biases b are added, then summation Σ may be represented by equation (3) below:

$$\Sigma = (x_1 w_1 + b_1) + (x_2 w_2 + b_2) + (x_3 w_3 + b_3) + (x_n w_n + b_n) \qquad (3)$$

The summation Σ may then be fed into an activation function $f$. The activation function $f$ may be any mathematical function suitable for calculating an output for the node. Example activation functions $f$ may include linear or non-linear functions, step functions such as the Heaviside step function, derivative or differential functions, monotonic functions, sigmoid or logistic activation functions, rectified linear unit (ReLU) functions, and/or leaky ReLU functions. The output of the function $f$ is then the output of the node. In a neural network with no hidden layers—such as the single-layer perceptron shown in FIG. 7—the output of the nodes in the output layer are the output variables or output vector of the neural network.

Figure 8:
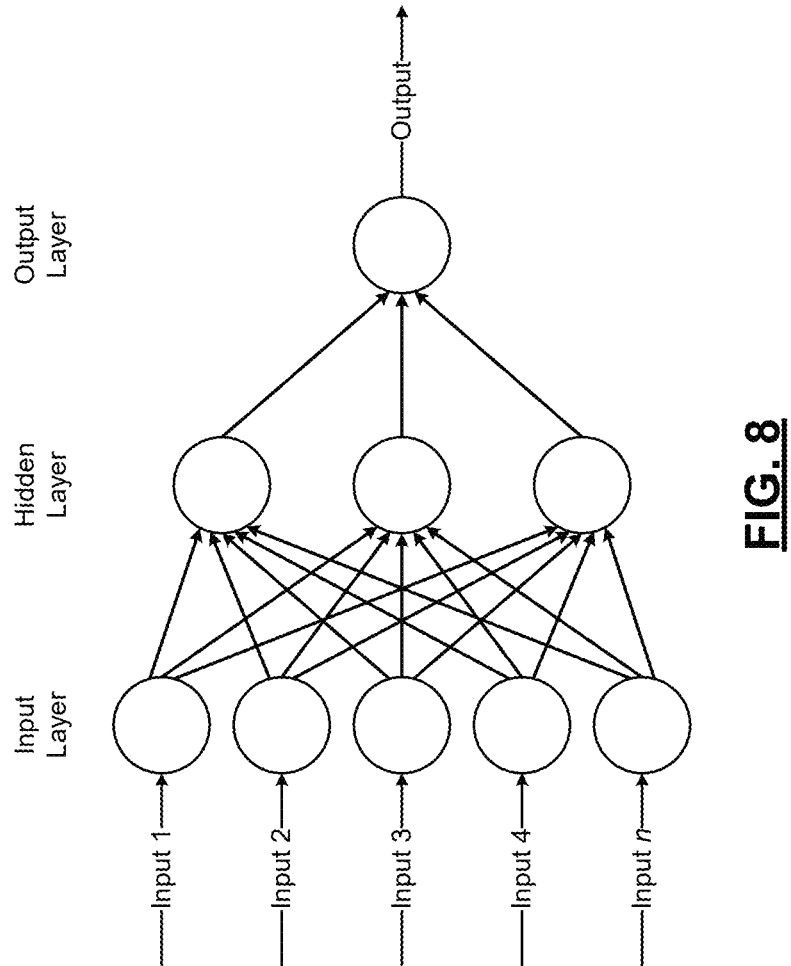
FIG. 8 is a functional block diagram of an example multi-layer neural network.

FIG. 8 is a graphical representation of an example neural network with one hidden layer for implementing the machine learning module. As illustrated in FIG. 8, the neural network may one or more intermediate layers—referred to as hidden layers—between the input layer and the output layer. The neural network of FIG. 8 may be referred to as a multilayer perceptron. Each node of a hidden layer may be connected to one or more nodes of the previous layer and receive inputs from the connected nodes of the previous layer—such as the value of the node of the previous layer multiplied by a weight ($x_n w_n$) or the value of the node of the previous layer multiplied by a weight with a bias added ($x_n w_n + b_n$). Each node of the hidden layer may then function in a manner analogous to the node of the output layer of FIG. 7 by summing the inputs, feeding the summed inputs into an activation function, and feeding the output of the activation function into one or more nodes of the next layer. Similarly, the nodes of the output layer function in a manner analogous to the node of the output layer of FIG. 7. For example, the nodes of the output layer may receive the outputs of the nodes of the previous layer (multiplied by a weight and/or with a bias added as desired) as inputs, sum the received inputs, feed the summed inputs to an activation function, and output the result of the activation function as an output of the neural network.

In various implementations, the neural network may have any number of hidden layers. In various implementations, each node of a previous layer may be connected to any number of nodes of a next layer. For example, as shown in FIG. 3, each node of the previous layer may be connected to each node of the next layer. Such a neural network may be referred to as a fully-connected neural network. In various implementations, each layer of the neural network may have any number of nodes. In various implementations, a neural network with no hidden layers may function as a linear classifier and be suitable for representing linearly separable decisions or functions. In various implementations, neural networks with one hidden layer may be suitable for performing continuous mapping from one finite space to another. In various implementations, neural networks with two hidden layers may be suitable for approximating any smooth mapping to any level of accuracy.

Figure 9:
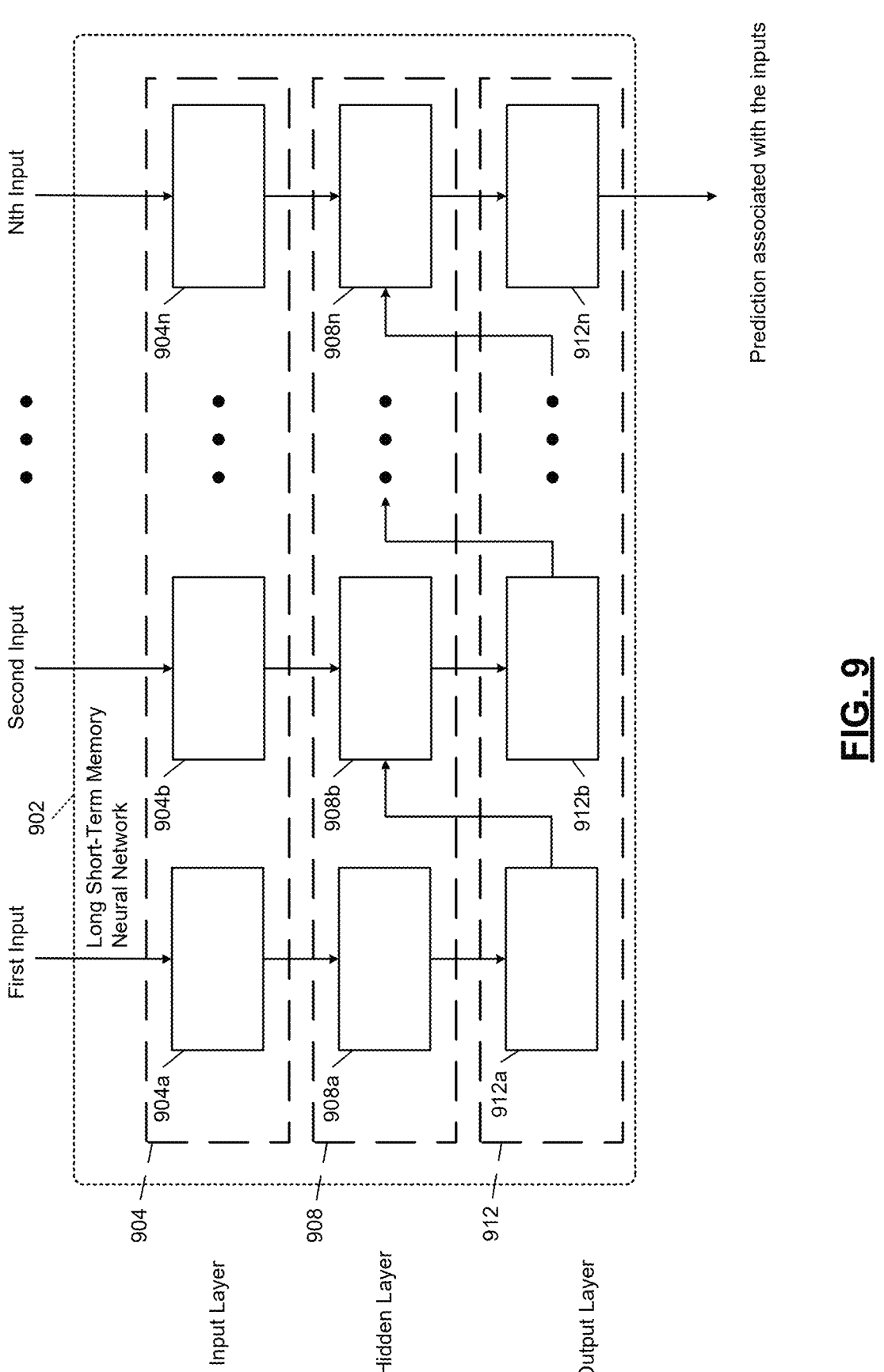
FIG. 9 is a functional block diagram of an example long short-term memory neural network.

FIG. 9 is a functional block diagram of an example neural network 902 that can be used to produce a predictive model. In some implementations, the neural network 902 can be a long short-term memory (LSTM) neural network. In some implementations, the neural network 902 can be a recurrent neural network (RNN). The example neural network 902 may be used to implement the machine learning as described herein, and various implementations may use other types of machine learning networks. The neural network 902 includes an input layer 904, a hidden layer 908, and an output layer 912. The input layer 904 includes inputs 904a, 904b . . . 904n. The hidden layer 908 includes neurons 908a, 908b . . . 908n. The output layer 912 includes outputs 912a, 912b . . . 912n.

Each neuron of the hidden layer 908 receives an input from the input layer 904 and outputs a value to the corresponding output in the output layer 912. For example, the neuron 908a receives an input from the input 904a and outputs a value to the output 912a. Each neuron, other than the neuron 908a, also receives an output of a previous neuron as an input. For example, the neuron 908b receives inputs from the input 904b and the output 912a. In this way the output of each neuron is fed forward to the next neuron in the hidden layer 908. The last output 912n in the output layer 912 outputs a probability associated with the inputs 904a-904n. Although the input layer 904, the hidden layer 908, and the output layer 912 are depicted as each including three elements, each layer may contain any number of elements. Neurons can include one or more adjustable parameters, weights, rules, criteria, or the like.

In various implementations, each layer of the neural network 902 must include the same number of elements as each of the other layers of the neural network 902. For example, training features may be processed to create the inputs 904a-904n.

The inputs 904a-904n can include data features (binary, vectors, factors or the like) stored in the storage device 110 or training data 420. The features can be provided to neurons 908a-908n for analysis and connections between the known facts. The neurons 908a-908n, upon finding connections, provides the potential connections as outputs to the output layer 912.

In some examples, a convolutional neural network may be implemented. Similar to neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer. In other words, input 904a is connected to each of neurons 908a, 908b . . . 908n.

The initial model that is built can be built in a secure environment using health data relating to patients. The initial model can then be refined based on feedback with a computing system that also is in a secure environment. The health data, e.g., the patient name, drug name, dosing data, and other prescription information, is always within a secure computing environment and not communicated out to a public data base and subjected to a third-party artificial intelligence. The secure computing system mitigates the risk of working with protected health data and other types of high-risk data, e.g., personal identifying information, and/or state protected data. In an example, the secure computing system is a mainframe computer with limited connection to external systems. In an example, the computing system is a private cloud environment that provides high-performance, secure, and flexible computing environments enabling the analysis of sensitive datasets restricted by federal privacy laws, proprietary access agreements, or confidentiality requirements. A private cloud environment can provide creation of any combination of network, CPU, RAM, and storage components into resource groups that can be used to build multi-tenant, multi-site infrastructure as a service.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in a different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship encompasses a direct relationship where no other intervening elements are present between the first and second elements as well as an indirect relationship where one or more intervening elements are present between the first and second elements.

As noted below, the term "set" generally means a grouping of one or more elements. However, in various implementations a "set" may, in certain circumstances, be the empty set (in other words, the set has zero elements in those circumstances). As an example, a set of search results resulting from a query may, depending on the query, be the empty set. In contexts where it is not otherwise clear, the term "non-empty set" can be used to explicitly denote exclusion of the empty set—that is, a non-empty set will always have one or more elements.

A "subset" of a first set generally includes some of the elements of the first set. In various implementations, a subset of the first set is not necessarily a proper subset: in certain circumstances, the subset may be coextensive with (equal to) the first set (in other words, the subset may include the same elements as the first set). In contexts where it is not otherwise clear, the term "proper subset" can be used to explicitly denote that a subset of the first set must exclude at least one of the elements of the first set. Further, in various implementations, the term "subset" does not necessarily exclude the empty set. As an example, consider a set of candidates that was selected based on first criteria and a subset of the set of candidates that was selected based on second criteria; if no elements of the set of candidates met the second criteria, the subset may be the empty set. In contexts where it is not otherwise clear, the term "non-empty subset" can be used to explicitly denote exclusion of the empty set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" can be replaced with the term "controller" or the term "circuit." In this application, the term "controller" can be replaced with the term "module." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); processor hardware (shared, dedicated, or group) that executes code; memory hardware (shared, dedicated, or group) that is coupled with the processor hardware and stores code executed by the processor hardware; other suitable hardware components that provide the described functionality; or a combination of some or all of the above, such as in a system-on-chip.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2020 (also known as the WIFI wireless networking standard) and IEEE Standard 802.3-2018 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

Some or all hardware features of a module may be defined using a language for hardware description, such as IEEE Standard 1364-2005 (commonly called "Verilog") and IEEE Standard 1076-2008 (commonly called "VHDL"). The hardware description language may be used to manufacture and/or program a hardware circuit. In some implementations, some or all features of a module may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

The memory hardware may also store data together with or separate from the code. Shared memory hardware encompasses a single memory device that stores some or all code from multiple modules. One example of shared memory hardware may be level 1 cache on or near a microprocessor die, which may store code from multiple modules. Another example of shared memory hardware may be persistent storage, such as a solid state drive (SSD) or magnetic hard disk drive (HDD), which may store code from multiple modules. Group memory hardware encompasses a memory device that, in combination with other memory devices, stores some or all code from one or more modules. One example of group memory hardware is a storage area network (SAN), which may store code of a particular module across multiple physical devices. Another example of group memory hardware is random access memory of each of a set of servers that, in combination, store code of a particular module. The term memory hardware is a subset of the term computer-readable medium.

The apparatuses and methods described in this application may be partially or fully implemented by a special-purpose computer created by configuring a general-purpose computer to execute one or more particular functions embodied in computer programs. Such apparatuses and methods may be described as computerized or computer-implemented apparatuses and methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special-purpose computer, device drivers that interact with particular devices of the special-purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The term non-transitory computer-readable medium does not encompass transitory electrical or electromagnetic signals propagating through a medium (such as on a carrier wave). Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The term "set" generally means a grouping of one or more elements. The elements of a set do not necessarily need to have any characteristics in common or otherwise belong together. The phrase "at least one of A, B, and C" should be construed to mean a logical (A OR B OR C), using a non-exclusive logical OR, and should not be construed to mean "at least one of A, at least one of B, and at least one of C." The phrase "at least one of A, B, or C" should be construed to mean a logical (A OR B OR C), using a non-exclusive logical OR.

The invention claimed is:

1. A method comprising:
receiving an indication that a user record associated with a user has been updated with a first change;
determining a confidence score that the first change is valid, wherein the confidence score does not meet a confidence threshold;
filtering a set of communications associated with the user to create a subset of communications, wherein filtering includes determining whether a respective communication of the set of communications includes a communication topic of the first change;
determining, via an analysis of the subset of communications by a first machine learning model, whether the first change has met one or more of a set of validity criteria, wherein:

a communication of the subset of communications includes a first portion, a second portion, and a third portion, and the first portion and the third portion are analyzed by the first machine learning model before the second portion is analyzed; and in response to a determination that the first change has not met the set of validity criteria:

based on a first outcome of a set of reporting criteria, automatically generating a prompt with a first suggested revision of the first change; and based on a second outcome of the set of reporting criteria, automatically revising the first change with the first suggested revision.

2. The method of claim 1 further comprising, based on the first outcome of the set of reporting criteria:

receiving a verification input corresponding to the prompt;

in response to a modification input corresponding to the prompt, revising the first suggested revision;

in response to an approval input corresponding to the prompt, accepting the first suggested revision; and in response to a rejection input corresponding to the prompt, rejecting the first suggested revision.

3. The method of claim 1 wherein:

the confidence score is determined by a second machine learning model;

the confidence score is based on a set of historical data associated with the user, including:

a current time of year, a level of novelty associated with the first change, a set of previous values associated with the user record, a set of dates associated with the set of previous values, and a quantity of deliveries associated with the set of previous values; and the method further comprises, updating a set of training data for the second machine learning model based on at least one of:

the confidence score, a user input corresponding to the prompt, or the first change.

4. The method of claim 1 wherein the filtering is performed by a third machine learning model.

5. The method of claim 1 further comprising, in response to a determination that the first change is valid:

generating an indication that the first change has been verified, and automatically generating and transmitting a report associated with the first change.

6. The method of claim 1 further comprising, in response to a determination that the confidence score has met a confidence threshold:

generating an indication that the first change has been verified, and automatically generating and transmitting a report associated with the first change.

7. The method of claim 1 further comprising digitizing the subset of communications, wherein digitizing the subset of communications includes at least one of:

transcribing a respective communication, performing an analysis via machine vision on the respective communication, translating the communication, processing text, audio, video, or image files, or performing optical character recognition.

8. The method of claim 1 wherein the set of reporting criteria includes:

a criterion that is met when a manufacturer associated with a product or service consumed by the user requires reports associated with the product or service to be transmitted to the manufacturer, a criterion that is met when user data must be changed by an authorized agent, and a criterion that is met when a user is associated with a product or service that meets a set of restriction requirements.

9. The method of claim 1 wherein the set of validity criteria includes:

a criterion that is met when a user requests the first change in a respective communication of the subset of communications, and a criterion that is met when the first change matches a set of data in the respective communication.

10. The method of claim 1 further comprising, in response to a determination that the first change has met the set of validity criteria, automatically preparing a physical product delivery.

11. The method of claim 1 wherein:

the first portion includes a beginning portion of the communication of the subset of communications, the second portion includes a middle portion of the communication of the subset of communications, and the third portion includes an end portion of the communication of the subset of communications.

12. A non-transitory computer-readable medium storing processor-executable instructions, wherein the instructions include:

receiving an indication that a user record associated with a user has been updated with a first change;

determining a confidence score that the first change is valid; and in response to a determination that the confidence score has not met a confidence threshold:

filtering a set of communications associated with the user to create a subset of communications, wherein filtering includes determining whether a respective communication of the set of communications includes a communication topic of the first change;

determining, via an analysis of the subset of communications by a first machine learning model, whether the first change has met one or more of a set of validity criteria, wherein:

a communication of the subset of communications includes a first portion, a second portion, and a third portion, and the first portion and the third portion are analyzed by the first machine learning model before the second portion is analyzed; and in response to a determination that the first change has not met the set of validity criteria:

based on a first outcome of a set of reporting criteria, automatically generating a prompt with a first suggested revision of the first change; and based on a second outcome of the set of reporting criteria, automatically revising the first change with the first suggested revision.

13. The non-transitory computer-readable medium of claim 12 wherein the instructions include, based on the first outcome of the set of reporting criteria:

receiving a verification input corresponding to the prompt;

in response to a modification input corresponding to the prompt, revising the first suggested revision;

in response to an approval input corresponding to the prompt, accepting the first suggested revision; and in response to a rejection input corresponding to the prompt, rejecting the first suggested revision.

14. The non-transitory computer-readable medium of claim 12 wherein:

the confidence score is determined by a second machine learning model;

the confidence score is based on a set of historical data associated with the user, including:

a current time of year, a level of novelty associated with the first change, a set of previous values associated with the user record, a set of dates associated with the set of previous values, and a quantity of deliveries associated with the set of previous values; and the instructions include, updating a set of training data for the second machine learning model based on at least one of:

the confidence score, a user input corresponding to the prompt, or the first change.

15. The non-transitory computer-readable medium of claim 12 wherein the instructions include, in response to a determination that the first change is valid:

generating an indication that the first change has been verified, and automatically generating and transmitting a report associated with the first change.

16. The non-transitory computer-readable medium of claim 12 wherein the set of reporting criteria includes:

a criterion that is met when a manufacturer associated with a product or service consumed by the user requires reports associated with the product or service to be transmitted to the manufacturer, a criterion that is met when user data must be changed by an authorized agent, and a criterion that is met when a user is associated with a product or service that meets a set of restriction requirements.

17. A system comprising:

memory hardware configured to store instructions; and processor hardware configured to execute instructions stored by the memory hardware, wherein the instructions include:

receiving an indication that a user record associated with a user has been updated with a first change;

determining a confidence score that the first change is valid; and in response to a determination that the confidence score has not met a confidence threshold:

filtering a set of communications associated with the user to create a subset of communications, wherein filtering includes determining whether a respective communication of the set of communications includes a communication topic of the first change;

determining, via an analysis of the subset of communications by a first machine learning model, whether the first change has met one or more of a set of validity criteria, wherein:

a communication of the subset of communications includes a first portion, a second portion, and a third portion, and the first portion and the third portion are analyzed by the first machine learning model before the second portion is analyzed; and in response to a determination that the first change has not met the set of validity criteria:

based on a first outcome of a set of reporting criteria, automatically generating a prompt with a first suggested revision of the first change; and based on a second outcome of the set of reporting criteria, automatically revising the first change with the first suggested revision.

18. The system of claim 17 wherein the instructions include, based on the first outcome of the set of reporting criteria:

receiving a verification input corresponding to the prompt;

in response to a modification input corresponding to the prompt, revising the first suggested revision;

in response to an approval input corresponding to the prompt, accepting the first suggested revision; and in response to a rejection input corresponding to the prompt, rejecting the first suggested revision.

19. The system of claim 17 wherein:

the confidence score is determined by a second machine learning model;

the confidence score is based on a set of historical data associated with the user, including:

a current time of year, a level of novelty associated with the first change, a set of previous values associated with the user record, a set of dates associated with the set of previous values, and a quantity of deliveries associated with the set of previous values; and the instructions include, updating a set of training data for the second machine learning model based on at least one of:

the confidence score, a user input corresponding to the prompt, or the first change.

20. The system of claim 17 wherein the instructions include, in response to a determination that the first change is valid:

generating an indication that the first change has been verified, and automatically generating and transmitting a report associated with the first change.

* * * * *